(12) United States Patent
Glassman et al.

(10) Patent No.: US 6,573,301 B1
(45) Date of Patent: Jun. 3, 2003

(54) CARBAMIDE PEROXIDE COMPOSITIONS FOR THE TREATMENT OF DERMATOLOGICAL DISORDERS AND METHODS FOR THEIR USE

(75) Inventors: Bradley P. Glassman, Fairfield, NJ (US); Dileep Bhagwat, Bronxville, NY (US); Daniel Glassman, Fairfield, NJ (US)

(73) Assignee: Bradley Pharmaceuticals, Inc., Fairfield, NJ (US)

( * ) Notice: Subject to any disclaimer, the term of this patent is extended or adjusted under 35 U.S.C. 154(b) by 0 days.

(21) Appl. No.: 10/128,674

(22) Filed: Apr. 23, 2002

(51) Int. Cl.⁷ ........................ A61K 31/17; A61K 31/075
(52) U.S. Cl. ........................................ 514/588; 514/714
(58) Field of Search ................................... 514/588, 714

(56) References Cited

U.S. PATENT DOCUMENTS

| | | | |
|---|---|---|---|
| 4,514,384 A * | 4/1985 | Gallina | 514/179 |
| 4,607,101 A * | 8/1986 | Bernstein | 514/24 |
| 4,853,998 A * | 8/1989 | Song et al. | 514/588 |
| 5,645,428 A * | 7/1997 | Yarborough | 433/215 |
| 5,919,470 A | 7/1999 | Valdez et al. | |
| 6,488,913 B2 * | 12/2002 | Orlowski et al. | 424/53 |

OTHER PUBLICATIONS

Application Ser. No. 09/961,623, filed Sep. 24, 2001.

* cited by examiner

Primary Examiner—William R. A. Jarvis
Assistant Examiner—Vickie Kim
(74) Attorney, Agent, or Firm—Merchant & Gould P.C.

(57) ABSTRACT

Topical compositions which include urea and carbamide peroxide are described. Compositions having a pH in the acidic range, particularly in the range of about 2.5 to about 9 are also described. Methods for treating dermatological disorders using the composition are also described.

2 Claims, No Drawings

CARBAMIDE PEROXIDE COMPOSITIONS FOR THE TREATMENT OF DERMATOLOGICAL DISORDERS AND METHODS FOR THEIR USE

FIELD OF THE INVENTION

This present disclosure relates to compositions containing carbamide peroxide and urea as components for the treatment of dermatological disorders.

BACKGROUND OF THE INVENTION

There is a need to provide carbamide peroxide compositions, which are easily and economically prepared, which have a smooth texture appropriate for cosmetic products, and which are enhanced by exhibiting greater keratolytic and antibacterial effects. Compositions having carbamide peroxide and urea as components might satisfy such a need because urea has keratolytic activity and has the property of denaturing and solubilizing proteins in addition to antimicrobial activity. However, urea containing formulations generally tend to be neutral to slightly alkaline, while carbamide peroxide formulations are generally most stable under acidic conditions.

SUMMARY

The present invention relates to a topical composition that combines the benefits of urea and carbamide peroxide and yet achieves a stable formulation. In one embodiment the topical composition comprises carbamide peroxide, urea, and a dermatologically acceptable carrier, wherein the composition has a pH between about 2.5 and about 9. In another embodiment the topical composition comprises about 0.5 to about 30% by weight carbamide peroxide, about 0.1 to about 40% urea by weight; and a dermatologically acceptable carrier.

The topical composition of the invention can be useful in treating dermatological disorders. Examples of dermatological disorders that can be treated by the composition include disorders due to changes in normal keratinization, epidermal formation or pilosebaceous function, such as acne, psoriasis, seborrhea, ingrown hairs and pseudofolliculitis barbae, and hyperpigmented skin.

In one embodiment, the invention provides a method for treating a dermatological disorder comprising administering to a subject in need thereof a topical composition of the invention.

DETAILED DESCRIPTION OF THE INVENTION

Overview

Carbamide peroxide and urea are pharmacological agents useful for the treatment of dermatological disorders. However, carbamide peroxide and urea have generally been considered incompatible. Carbamide peroxide can be extremely unstable. Thus, stability of carbamide peroxide is an important factor in formulating compositions containing carbamide peroxide. Carbamide peroxide formulations are generally most stable under acidic conditions. However, urea containing formulations generally tend to be neutral to slightly alkaline.

The novel compositions disclosed herein combine the benefits of urea and carbamide peroxide and yet achieve a stable formulation. In one embodiment, such a composition is achieved by use of an optimized buffer system that maintains the pH of the formulation at an optimal acidic range.

Topical Composition

The invention provides topical compositions comprising carbamide peroxide and urea. The desired amount of urea and carbamide peroxide can vary from composition to composition depending on the particular disorder or disorders being treated, the severity of the disorder, the duration of the treatment, the other specific components of the composition being used, and like factors. In one embodiment, the carbamide peroxide can be present in the composition at a concentration from about 0.5% to about 30% by weight and the urea can be present from about 0.1% to about 40% by weight, relative to the weight of the composition. In another embodiment, the carbamide peroxide can be present in the composition at a concentration from about 4 to about 15% by weight. In yet another embodiment, the carbamide peroxide can be present in the composition from about 4.5% to about 9% by weight. In still another embodiment, the urea can be present from about 5% to about 20% by weight, relative to the weight of the composition.

In one embodiment, the compositions of the invention are acidic. Carbamide peroxide is generally most stable under acidic conditions, while urea containing formulations generally tend to be neutral to slightly alkaline. As disclosed herein, acidic compositions including both carbamide peroxide and urea tend to be more stable under acidic conditions. In addition to allowing formation of a stable composition, a pH in an acidic range is also therapeutically useful. Generally, traumatized skin tends to have a higher pH and skin healing is aided by maintaining a slightly acidic pH. Thus, the novel formulations of this invention combine the benefits of urea and carbamide peroxide and yet achieve a stable formulation by the use of an optimized buffer system which maintains the pH of the formulation at an optimal acidic range. According to one embodiment of the invention, the composition has a pH less than 9. In another embodiment, the compositions have a pH in the range of about 2.5 to about 9.

Any dermatologically acceptable carrier can be used in the compositions of the invention. As used herein, "dermatologically acceptable carrier" refers to vehicles, diluents, carries, which can include adjuvants, additives, or excipients, known for use in dermatological compositions. The compositions of the invention include, but are not limited to, creams, ointments, solutions, lacquers, sticks, pledgets, wipes, cleansers and/or gels.

In one embodiment, the topical composition is a semi-solid at room temperature but is easily absorbed into the stratum corneum. The semi-solid composition can be a cream. Such a composition can include petroleum-based liquids and solid fractions as skin protectants. The solid skin protectant can be semi-solid. The solid skin protectant can be present in about 1.0% to about 20% in the composition and includes petrolatum or a synthetic or semi-synthetic hydrocarbon of the same nature as petrolatum. Mixtures of such ingredients can also be used. Liquid skin protectants can be petrolatum and contained in the composition in about 1.0% to about 20% and include any synthetic or semi-synthetic oleaginous liquid fraction. The liquid skin protectant can be mineral oil, which is a liquid mixture of hydrocarbons obtained from petroleum.

The compositions of the invention can include propylene glycol. Propylene glycol can be present in the composition up to about 5%. In one embodiment, propylene glycol is present in the composition at about 1% to about 5%.

The compositions can contain conventional preservatives, such as methyl paraben, propyl and butyl imidazolidinylurea, diazolidinylurea, methylchloroisothiazolinone and methylisothiazolinone. Although not to be held by theory, it is believed that the antibacterial properties of the urea and carbamide peroxide and propylene glycol allow the composition of the present invention to be free of conventional preservatives.

The present compositions can also contain dermatologically acceptable excipients, such as for example emulsifiers and thickeners. Among these are for example $C_{16}$ to $C_{18}$ straight or branched chain fatty alcohols or fatty acids or mixtures thereof. Examples of emulsifiers and thickeners include cetyl alcohol, stearyl alcohol, stearic acid, palmitic acid, nor mixtures thereof. Fatty acids or fatty alcohols may be present in from about 0.25 to 2 wt-%.

Another ingredient useful in the composition of the present invention may be glyceryl stearate, which is a monoester of glycerine and stearic acid, or other suitable forms of glyceryl stearate for example glyceryl stearate SE, which is a commercially available self-emulsifying grade of glycerol stearate that contains some sodium and/or potassium stearate. Glyceryl stearate may be in the composition anywhere from about 1 to about 3% by weight.

Xanthan gum is another ingredient which may be used in the present compositions. Xanthan gum is a high molecular weight heteropolysaccharide gum produced by pure-culture fermentation of a carbohydrate with Xanthomonas campestris. The gum is also commercially available from various sources.

The composition can be an emulsion including liposomes. The emulsion can contain a fatty phase in the range of about 5% to about 80% by weight. Typically, the fatty phase will range from about 5% to about 50% by weight, with respect to the total weight of the composition. Known oils, waxes, emulsifiers and coemulsifiers can be used in compositions in the emulsion form. The emulsifier and the coemulsifier can be present, in the composition, in a proportion ranging from about 0.3% to about 30% by weight. Typically the emulsifier and the coemulsifier are present in a proportion ranging from about 0.5 to about 20% by weight. The emulsion can also contain lipid vesicles.

In one embodiment, the composition can include thickeners which provide a high viscosity cream designed to remain in place upon application to the skin. By way of example, thickeners can include a mixture of a carbomer and triethanolamine. The mixture can be combined together and added to the composition in an amount totaling anywhere from about 0.05 to 30% by weight. Triethanolamine can be purchased as Trolamine NF from BASF. Carbomers come in various molecular weights and are identified by numbers. These are otherwise known as Carbopol. Exemplary Carbopols include is Carbopol 940, 910, 2984, 5984, 954, 980, 981, 941 and 934. Carbopol ETD 2001, 2020, and 2050 and Ultrez 20 are also commercially available and can be used. The carbomer or Carbopols are resins which are known thickening agents. They are homopolymers of acrylic acid crosslinked with an allyl ether of pentaerythritol, an allyl ether of sucrose or an allyl ether of propylene. The carbomer can be present in the composition as a thickener and also can be used to suspend and stabilize the emulsion.

The composition can also contain known adjuvants and additives, such as bactericides, fungicides, virucides, light filter substances, active ingredients with a cooling action, antioxidants, plant extracts, anti-inflammatories, substances which promote wound healing, skin-lightening agents, screening agents, odor absorbers, skin-coloring agents, perfumes, antifoams, dyes, pigments which have a coloring action, thickeners, surface-active substances, emulsifiers, emollients, moisturizers and/or humectants, fats, oils, waxes, alcohols, polyols, polymers, foam stabilizers, electrolytes, organic solvents, silicone derivatives or chelating agents. These additives and adjuvants, depending on their nature, can be introduced into the fatty phase, into the aqueous phase and/or into the lipid spherules.

Exemplary oils or waxes suitable for use in the compositions include mineral oils (liquid petrolatum), vegetable oils (liquid fraction of karite butter, sunflower oil), animal oils (perhydrosqualene), synthetic oils (purcellin oil), silicone oils or waxes (cyclomethicone) and fluorinated oils (perfluoropolyethers), beeswax, carnauba wax or paraffin wax. Fatty alcohols and fatty acids (stearic acid) can be added to these oils.

Exemplary emulsifiers which are suitable include glyceryl stearate, polysorbate 60 and the PEG-6/PEG-32/glycol stearate mixture marketed under the trademark Tefose.RTM. 63 by Gattefosse.

Exemplary solvents which can be used in the compositions include the lower alcohols, such as ethanol, isopropanol, acetone and propylene glycol.

Exemplary hydrophilic gelling agents suitable for use in the compositions include carboxyvinyl polymers (carbomer), acrylic copolymers such as acrylate/alkyl acrylate copolymers, polyacrylamides, polysaccharides such as hydroxypropylcellulose, natural gums and clays. And exemplary lipophilic gelling agents include modified clays such as bentones, metal salts of fatty acids such as aluminum stearates, and hydrophobic silica, ethylcellulose or polyethylene.

The compositions can contain other hydrophilic active principles, such as proteins or protein hydrolysates, amino acids, polyols, urea, allantoin, sugars and sugar derivatives, water-soluble vitamins, plant extracts, e.g. aloe and hydroxy acids.

Representative lipophilic active principles include retinol (vitamin A) and derivatives thereof, tocopherol (vitamin E) and derivatives thereof, essential fatty acids, ceramides, essential oils or salicylic acid and derivatives thereof.

Suitable antioxidants that can be used in the compositions include tocopherols (vitamin E), tocopherol derivatives, tocotrienols, ascorbic acid (vitamin C), ascorbic acid derivatives, carotenoids, vitamin A or derivatives thereof, butylated hydroxytoluene, butylated hydroxyanisole, gallic esters, flavonoids such as, for example, quercetin or myricetin, catechins such as, for example, epicatechin, epicatechingallate, epigallocatechin or epigallocatechingallate, sulfur-containing molecules such as, for example, glutathione, cysteine, lipoic acid, N-acetylcysteine, chelating agents such as, for example, ethylenediamine tetraacetic acid or other customary antioxidants. Antioxidants can be included in the compositions at about 0.0001 to about 30% by weight. Typically antioxidants will be included from about 0.0001 to about 20% by weight. Most often antioxidants will be included from about 0.0001 to about 5% by weight, based on the total weight of the preparation.

Additional antibiotic agents can be included in the compositions of the invention. Preferably the antibiotics are dermatologically absorbable. Suitable dermatologically absorbable antimicrobial, antibiotic, antibacterial or antifungal agents include erythromycin, bacitracin, zinc bacitracin, polymycin, neomycin, chloramphenicol, tetracycline, minocycline, clindamycin, doxycycline, undecylenic acid and salts thereof, propionic acid and salts thereof, caprylic acid and salts thereof, ciprofloxacin, cephlasporins, benzoic acid, ciclopiroxolamine, clotrimazole, econazole nitrate, metronizadole, miconazole nitrate, ketacanazole, oxiconazole, tolnaftate.

Antifungal agents can also be included in the compositions of the invention. These include, for example, amoroline, betadine, bifonazole, clotrimazole, econazole nitrate, isoconazole, ketoconazole, miconazole nitrate, naftifine hydrochloride, oxiconazole, sulfanazole, terbinafine, ticonazole, tolnaftate, and undecenoates.

Additional keratolytic agents such as salicylic acid and alpha hydroxy acids can be included in the composition.

Dermatological Disorders

The invention provides a method for treating a dermatological disorder comprising administering to a subject in need thereof a topical composition of the invention. As used herein, "treating" or "treatment" means the prevention or reduction of severity of symptoms or effect of a dermatological disorder. A "subject" according to the invention refers to any multicellular organism having skin. Typically, the subject will be a mammal, such as a mouse, a rat, a pig, a horse, a cat, a dog, an elephant, a giraffe, a monkey, or a human, and the like. Typically, the mammal will be a human.

The term "administering" as used herein refers to any method which, in sound medical practice, delivers the composition to a subject in such a manner to so as to be effective in the treatment of a dermatological disorder. The compositions are preferably administered such that they cover the entire area to be treated.

The phrase "safe and effective amount", as used herein, means an amount of a composition or component thereof sufficient enough to positively modify the disorder to be treated but low enough to avoid serious side effects, within the scope of sound medical advice. Safe and effective amounts will vary with the particular disorder or disorders being treated, the severity of the disorder, the duration of the treatment, the specific components of the composition being used, and like factors as are known by health-care providers, including physicians.

As used herein, "dermatological disorder" refers to any disorder of skin, hair, or glands. A dermatological disorder can be manifest in the form of visible lesions, pre-emergent lesions, pain, sensitivity to touch, irritation, inflammation, or the like. Dermatological disorders include disorders of the cutaneous and pilosebaceous unit or the process of keratogenesis. For example, a dermatological disorder can be a disorder of the epidermis or dermis, or within and surrounding the pilosebaceous follicle, which is located within the skin's epidermis, dermis, or both. Examples of dermatological disorders include acne, psoriasis, seborrhea, ingrown hairs and pseudofolliculitis barbae, and hyperpigmented skin, cutaneous infections, and the like.

The invention provides a composition comprising carbamide peroxide and urea. Accordingly, the compositions can be useful for treating dermatological disorders for which carbamide peroxide or urea are known to be useful. Urea has been long recognized as a cosmetic ingredient in formulations acting as a humectant and moisturizer. Urea also has keratolytic activity and has the property of denaturing and solubilizing proteins. Additionally, it has been found that urea has mild antimicrobial activity. Carbamide peroxide has been employed as a keratolytic drug and as an antibacterial agent in the past, but is mostly used in to soften earwax. The combination of urea and carbamide peroxide provides synergistic antimicrobial activity. Keratolytic agents are agents that can remove or sluff dead cells of the horny outer layer of the skin (stratus corneum), which are composed largely of keratin. Such agents can prevent obstruction of follicular ducts or reopen obstructed ducts. Thus, the compositions can be useful for treating dermatological disorders in which a humectant, moisturizer, keratolytic agent, antibacterial agent, protein denaturant or solubilizer, or a combination thereof would be beneficial. Such disorders include any disorder involving obstruction of a follicular duct or bacterial infection. In addition, carbamide peroxide has been useful, and thus the compositions of the invention would be useful, in the topical treatment of skin lesions such as acne, burns, varicose ulcers, sycosis vulgaris, seborrhea and rosacea.

The compositions of the invention can also be used to treat dermatological disorders resulting in visible lesions. Examples of such disorders include acne, cutaneous infections, psoriasis and other disorders of the cutaneous and pilosebaceous unit or the process of keratogenesis. Visible lesions include closed comedones, open comedones, red or pustular-looking inflamed papules, pustules, nodules and cysts of acne or cutaneous infection; visible ingrown hairs of pseudofolliculitis barbae; visible scales of seborrhea, ichthyosis and psoriasis; and the like. Visible lesions can be due to obstruction of follicular ducts, thickened sebum, bacterial infection, or a combination thereof. Accordingly, the compositions can be used to prevent obstruction of follicular ducts, to reopen a duct if it has become blocked, to combat thickened sebum, to combat bacterial infection, or a combination thereof Treatment of visible lesions can be evaluated based on the effectiveness of the treatment in reducing the number and severity of visible lesions. Any reduction in number or severity of visible lesions as a result of administration a composition would be considered treatment of visible lesions.

In one embodiment, the compositions of the invention can be used to treat pre-emergent lesions. As used herein, "pre-emergent lesions" refers to non-visible lesions present within the skin prior to eruption of visible lesions on the surface of the skin. Like visible lesions, pre-emergent lesions can be due to obstruction of follicular ducts, thickened sebum, bacterial infection, or a combination thereof. Accordingly, the compositions can be used to treat pre-emergent lesions by preventing obstruction of follicular ducts, reopening a duct if it has become blocked, combating thickened sebum, combating bacterial infection, or a combination thereof While pre-emergent lesions are insufficiently visible to be graded in conventional clinical studies, their presence within the skin can be discerned by the tactile sense of feel and/or by pain and tension within the skin. Any reduction in number of locations within the skin in which pre-emergent lesions exist as a result of administration of a composition would be considered treatment of pre-emergent lesions. Similarly, any reduction in the severity of the symptoms of a pre-emergent lesion as a result of administration of a composition would be considered treatment of the pre-emergent lesion.

In another embodiment, the compositions of the invention can be used to treat acne. As used herein, "acne" means a disorder of the skin caused by inflammation of skin glands or hair follicles. The compositions of the invention can be used to treat acne at early pre-emergent stages or later stages where lesions from acne are visible. Early pre-emergent stages of acne usually begins with an excessive secretion of sebum or dermal oil from the sebaceous glands located in the pilosebaceous apparatus. Sebum reaches the skin surface through the duct of the hair follicle. The presence of excessive amounts of sebum in the duct and on the skin tends to obstruct or stagnate the normal flow of sebum from the follicular duct, thus producing a thickening and solidification of the sebum to create a solid plug known as a comedone. In the normal sequence of developing acne, hyperkeratinazation of the follicular opening is stimulated, thus completing blocking of the duct. The usual results are papules, pustules, or cysts, often contaminated with bacteria, which cause secondary infections. Acne is characterized particularly by the presence of comedones, inflammatory papules, or cysts. The appearance of acne may range from slight skin irritation to pitting and even the development of disfiguring scars. Accordingly, the compositions of the invention can be used, but not limited, to treat skin irritation, pitting, development of scars, comedones, inflammatory papules, cysts, hyperkeratinazation, and thickening and hardening of sebum associated with acne.

All patent and literature references cited in the present specification are hereby incorporated by reference in their entirety. All parts and percentages are by weight unless otherwise specified. All scientific and technical terms used in this application have meanings commonly used in the art unless otherwise specified.

EXAMPLES

The following examples are offered for illustrative purposes only, and are not intended to limit the scope of the present invention in any way.

Example 1

Preparation of Formula I, an Exemplary Composition

Formula I is composed of the ingredients shown in Table 1 and is prepared using the following protocol.

TABLE 1

| | Component | Weight Percent |
|---|---|---|
| A. | Hydrous Carbamide Peroxide (milled) | 15.0% |
| | Propylene Glycol | 3.0% |
| | Purified Water | 8.0% |
| B. | PEG 75 | 5.0% |
| | Glyceryl Stearate | 5.0% |
| | Cetyl Alcohol | 5.0% |
| | White Petroleum | 5.0% |
| | Polysorbate 60 | 2.0% |
| | Sorbitan Mono Stearate | 1.0% |
| C. | Purified Water | 36.0% |
| | Citric Acid | 2.0% |
| | Urea | 10.0% |
| | Xanthan Guan | 0.5% |
| | Aloe Vera Aqueous Extract Concentrate | 1.0% |
| D. | Sodium Hydroxide (10% Solution) to | pH 4–8.) |
| E. | Purified Water QS (quantity sufficient) | 100.0% |

Method

1. In the main mixing tank place components of B. and heat to 75° C. and mix.
2. Separately dissolve Citric Acid and Urea in Purified Water (C) and disperse Xanthan Gum and Aloe Concentrate. Let stand.
3. From Step 2 heat to about 75° C. into main tank while mixing. Homogenize then cool.
4. Separately combine (A) components carefully and warm to 50–55° C. and add to main tank when it has cooled to 50–55° C. and continue to mix.
5. Add D to main tank to adjust pH to 4.0–6.0.
6. Add Purified Water to QS the batch.

Example 2

Preparation of Formula II, an Exemplary Composition

Formula II is composed of the ingredients shown in Table 2 and is prepared using the following protocol.

TABLE 2

| | Component | Weight Percent |
|---|---|---|
| A. | Hydrous Carbamide Peroxide (milled) | 15.0% |
| | Propylene Glycol | 5.0% |
| | Glycerine | 10.0% |
| | Purified Water | 10.0% |
| B. | Triethanolamine | 1.50% |
| | Purified Water | 10.0% |
| C. | Purified Water | 10.0% |
| | Carbomer 940 | 1.5% |
| | Citric Acid | 2.0% |
| | Urea | 10.0% |
| D. | Aloe Vera Aqueous Extract Concentrate | 1.0% |
| E. | Purified Water QS | 100.0% |

Method

1. Place components of C in the main mixing tank as follows. To the Purified Water add urea, citric acid and mix to dissolve. Then disperse the Carbomer 940 and mix. Let stand.
2. Separately, (carefully) combine the components A in a mixing tank, mill to smooth consistency and mix.
3. While mixing add A (Step 2) to the main tank.
4. Separately combine components of B and add to the main tank. Continue to mix carefuilly.
5. Add Aloe concentrate to the batch and continue to mix
6. Add Purified Water (D) to QS the batch.

Although the present invention has been described in terms of specific embodiments, changes and modifications can be carried out without departing from the scope of the invention which is intended to be limited only by the scope of the appended claims.

We claim:

1. A method for treating a dermatological disorder comprising administering to a subject in need thereof a topical composition comprising:

(a) about 0.5 to about 30 weight % carbamide peroxide;

(b) about 0.1 to about 40 weight % urea; and (c) a dermatologically acceptable carrier, wherein the dermatological disorder is selected from the group consisting of acne, psoriasis, seborrhea, ingrown hairs, pseudofolliculitis barbae, hyperpigmented skin, and cutaneous infection.

2. The method of claim 1, wherein the dermatological disorder is acne.

* * * * *